United States Patent
Arnold

(10) Patent No.: US 6,679,432 B1
(45) Date of Patent: Jan. 20, 2004

(54) AUDIBLE INDICATION OF DISCONNECTION BETWEEN A CONVECTIVE DEVICE AND AN AIR HOSE IN A CONVECTIVE WARMING SYSTEM

(75) Inventor: Randall Charles Arnold, Minnetonka, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 0 days.

(21) Appl. No.: 10/214,952

(22) Filed: Aug. 8, 2002

(51) Int. Cl.[7] .................................................. A01K 31/20
(52) U.S. Cl. .............................. 237/3; 237/14; 607/96; 604/113; 128/202.22
(58) Field of Search .................... 237/3, 14; 607/96, 607/98; 128/202.22; 604/113

(56) References Cited

U.S. PATENT DOCUMENTS

| | | | |
|---|---|---|---|
| 1,395,431 A | * 11/1921 | Kresky | .......................... 237/3 |
| 3,595,228 A | * 7/1971 | Simon et al. | .......... 128/202.22 |
| 4,067,329 A | * 1/1978 | Winicki | ................. 128/202.22 |
| 4,302,640 A | 11/1981 | Vicenzi et al. | |
| 4,316,182 A | 2/1982 | Hodgson | |
| 5,057,822 A | 10/1991 | Hoffman | |
| 5,300,098 A | 4/1994 | Philpot | |
| 5,300,101 A | 4/1994 | Augustine et al. | |
| 5,300,102 A | 4/1994 | Augustine et al. | |
| 5,320,092 A | 6/1994 | Ryder | |
| 5,324,320 A | 6/1994 | Augustine et al. | |
| 5,356,531 A | * 10/1994 | Rantz | .......................... 210/86 |
| 5,405,371 A | 4/1995 | Augustine et al. | |
| 5,626,129 A | 5/1997 | Klimm et al. | |
| 5,661,231 A | * 8/1997 | Koskela | ...................... 73/49.8 |
| 5,706,801 A | 1/1998 | Remes et al. | |
| 5,785,723 A | 7/1998 | Beran et al. | |
| 5,807,332 A | 9/1998 | Augustine et al. | |
| 5,816,186 A | 10/1998 | Shepherd | |
| 5,865,171 A | 2/1999 | Cinquin | |
| 5,881,717 A | 3/1999 | Isaza | |
| 5,950,621 A | 9/1999 | Klockseth et al. | |
| 6,126,393 A | 10/2000 | Arnold | |
| 6,126,681 A | 10/2000 | Van Duren et al. | |
| 6,143,020 A | 11/2000 | Shigezawa et al. | |
| 6,309,408 B1 | 10/2001 | Arnold et al. | |
| 6,357,491 B1 | 3/2002 | Buchanan et al. | |
| 6,386,196 B1 | * 5/2002 | Culton | ................... 128/205.23 |

FOREIGN PATENT DOCUMENTS

| | | |
|---|---|---|
| JP | 08322959 | 12/1996 |
| WO | WO 00/06904 | 10/2000 |

OTHER PUBLICATIONS

EN–60601–2–35–1996 E: European Standard for medical electrical equipment, heating blankets, heating pads, heating mattresses, safety requirements, protection against electric shock, protection against mechanical hazard, radiation protection, fire protection, environmental conditions adopted by CENELEC, European Committee for Electrotechnical Standardization.
ASTMF29.19 Subcommittee for Patient Warming Equipment, "Standard Specification for Circulating Liquid and Forced Air Patient Temperature Management Devices".
PCT Search Report for PCT/US99/07567.

* cited by examiner

Primary Examiner—Derek Boles
(74) Attorney, Agent, or Firm—Incaplaw; Terrance A. Meador

(57) ABSTRACT

In a convective treatment system a wind-actuated instrument mounted near an end of an air hose provides, generates, issues, or sounds an audible alarm when the end becomes disconnected from a convective device and pressurized air continues to flow through the end. The instrument may be mounted on an interface device receivable on the end. The interface device may include means for reducing or stopping the flow of air through the end in response to the disconnection.

9 Claims, 6 Drawing Sheets

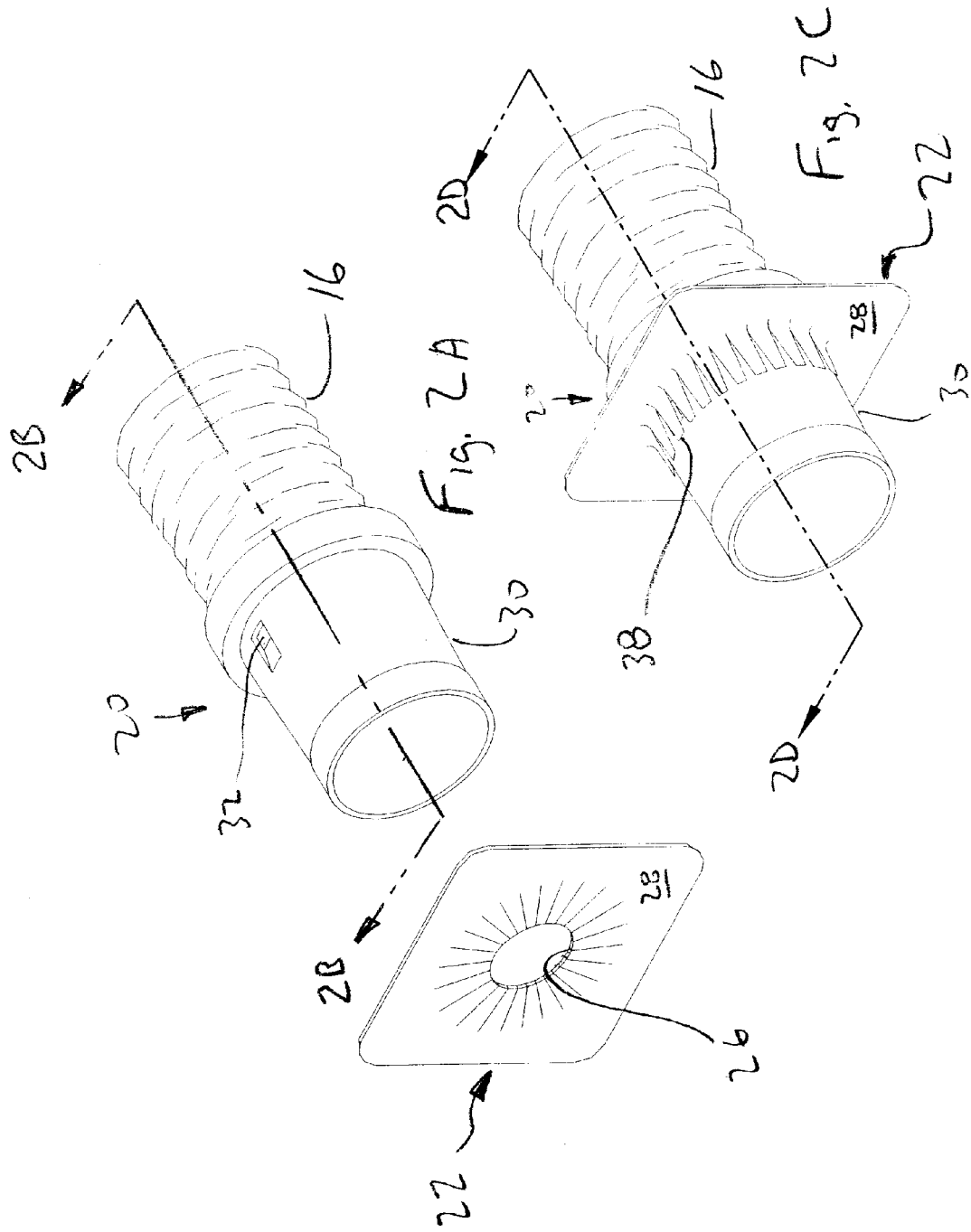

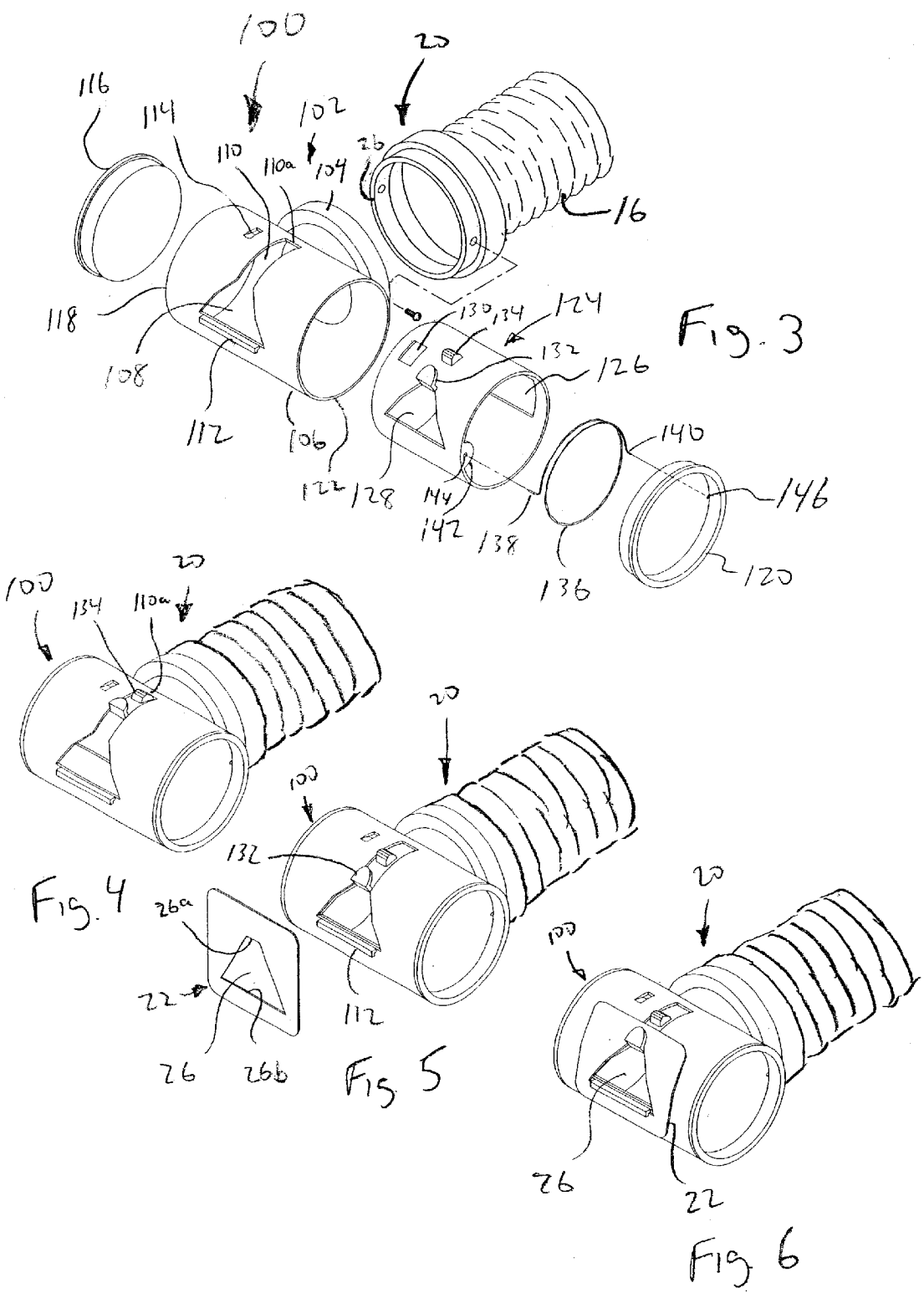

AUDIBLE INDICATION OF DISCONNECTION BETWEEN A CONVECTIVE DEVICE AND AN AIR HOSE IN A CONVECTIVE WARMING SYSTEM

FIELD OF THE INVENTION

This invention relates generally to safety measures in the convective treatment of persons. The invention also relates to audibly indicating a condition threatening injury to a person during convective treatment. Such a condition might occur when an air hose is disconnected from a convective device, which can pose the danger of injury resulting from discharging pressurized, thermally-conditioned air from the air hose directly onto the person.

BACKGROUND OF THE INVENTION

A convective treatment system typically consists of at least a temperature-control/blower unit (known simply as a "blower"), a ducting system, and a convective device such as a convective warming blanket. A blower aspirates air from an ambient environment, changes its temperature to a desired value, pressurizes the air above the ambient pressure, and discharges the air at an exhaust port. U.S. Pat. No. 6,126,393 describes such a blower and associated temperature and noise control schemes. In an exemplary convective treatment system, pressurized, thermally regulated air produced by a blower is conveyed through a ducting system and delivered to a convective device, such as a convective warming blanket, that distributes the thermally regulated air around a person or a specific body area of a person. Such treatment is frequently used, for management or modulation of the person's body. core temperature. For example, convective thermal treatment is particularly effective in preventing or mitigating hypothermia.

A convective device may be embodied, for example, in an inflatable device which inflates with pressurized, thermally regulated air and has one or more surfaces adapted for expelling air onto a person. Such devices may lie on, around, or under the person. A convective device is generally realized as a blanket, but can be embodied by other appliances or attachments that are designed to be operated by or with the application of pressurized, thermally conditioned air. When used herein, the term "convective device" is intended to include all blankets, pads, covers, manifolds, and equivalent structures that operate as just described. Irrespective of orientation, a convective device utilized for convective thermal treatment of persons performs at least three basic functions. These functions are 1) the conveyance of thermally conditioned air from at least one inlet port into the device, 2) the imposition of a heat gain or loss that changes the temperature of the thermally conditioned air, and 3) the extravasation of the thermally conditioned air from the device. In the following discussion, the assumption is that such a convective treatment device is operated to warm a person by delivery of heat to the person.

In those convective treatment systems which treat a person by the application of heat, heat may be transferred by convection, radiation, and conduction, but convection generally predominates at the interface between the convective device and the person. The rate of convective heat transfer depends on material properties, surface boundary conditions, and significantly, fluid velocity.

Heat is lost from a convective treatment system whenever a temperature gradient exists between it and the ambient environment. During normal operation of the system, the temperature of the air expelled onto the person is maintained at a level that is generally higher than the person's skin surface temperature, but not high enough to cause tissue damage. In order to counter the loss of heat from the system, however, the air is heated initially to a temperature that may exceed the thermal damage threshold at the target site on the person's skin. Within certain limits, the amount of heat lost from the system is predictable. This predictability allows the system to operate safely by measuring and controlling the temperature at the proximal end of the air supply duct that connects the blower to the convective device. If any factors upon which the assumption of predictability depends are altered, however, the fluid temperature at the distal end of the duct system may be affected.

Several intrinsic and extrinsic factors contribute to the rate of heat loss from a convective treatment system. Among the intrinsic factors are the surface area and material characteristics of the duct and convective device, and the residence time of the warmed air within the duct and convective device. Extrinsic factors include, but are not limited to, ambient temperature and air velocity in the area immediately adjacent to the duct and the convective device. The residence time of the heated fluid within the system is a function of its pressure and the resistance exerted by the entire system. Factors that influence resistance are the duct diameter and length, the orientation of the duct, and the resistance of the convective device or devices.

One hazard associated with the use of convective treatment is burns. First-, second-, and third-degree burns have occurred through the improper use of convective treatment systems. The bum hazard is accentuated by the intentional or accidental alteration of the intrinsic or extrinsic factors that moderate the heat loss in the system. The alteration of any of these factors introduces an unpredictable amount of heat loss into the system, which can significantly alter the temperature or velocity of the heated air delivered to the person. One of the more important factors that influence the temperature of warm air flowing out of the air supply duct through the end where it connects to the convective device is the residence time of the air within the duct. The end through which air flows out of the air supply duct is usually referred to as the "distal end" of the air supply duct. Typically, a nozzle may be mounted to this end. The temperature of pressurized warm air exiting the duct at this end is called "nozzle temperature" (whether or not a nozzle is mounted thereto). In general, a decrease in residence time of the pressurized warmed air is usually associated with an increase in the nozzle temperature of the air.

In the field, a common misuse of one or more components of a convective treatment system may occur. Either intentionally or accidentally, some users fail to connect the convective device to the distal end of the duct and allow the heated air discharged from the distal end to make direct contact with the person. In view of the fact that an air supply duct is typically embodied as an air hose, this practice has come to be known as "hosing" or "free-hosing." In other cases, operators have failed to connect the convective device to the duct and allowed the heated duct to make direct contact with the person's skin. In still other cases, frequent handling, careless assembly, movement of equipment, and other factors, alone or in combination, may cause the convective device to become wholly or partly disconnected from the duct. Users who have experienced therapeutic misadventures through this type of misuse and/or mistake have reported their experiences of thermal injuries to the FDA and the manufacturers of the offending convective treatment systems. Some manufacturers of have responded by warning and training users and affixing labels to the thermal-control/blower units and convective devices. Despite warnings, training, and labeling, however, persons continue to be injured through misuse of warming devices.

The American Society for Testing and Materials (ASTM) has recently circulated a draft standard (ASTM F29.19.01) from the Subcommittee for Patient Warming Equipment entitled Standard Specification for Circulating Liquid and Forced Air Patient Temperature Management Devices. The members of the ASTM subcommittee recognized the hazards associated with the practice of free-hosing and developed requirements for equipment to limit skin surface temperatures to 48° C., or manufacturers of thermal-control/blower units to affix a cautionary statement to the distal end of the air supply duct that warns the user against the practice of "free-hosing." Thus, the ASTM standard explicitly recognizes the importance of air temperature, and tacitly acknowledges the role of airflow, in causing thermal burns.

Hosing causes at least four uniquely hazardous conditions to exist: 1) The loss of the resistance from the lack of an convective device leads to a decrease in the residence time of warmed air in the air supply duct. As the warmed air has less time to cool in the air supply duct, it arrives at the distal end of the duct at a higher than normal temperature; 2) The lack of airflow resistance from the absence of the convective device also leads to an increase in the air velocity and quantity of air that is exhausted from the supply duct; The relative increase in air velocity can lead to significantly higher heat transfer rates if the air strikes the skin; 3) The lack of a convective device makes it possible for the high temperature and high velocity air to strike directly the person's skin over a very small area. In essence, all, or most, of the heat energy intended to be distributed over a large surface area is concentrated onto a very small area; and 4) The lack of a convective device makes it possible for the air supply duct itself to make direct contact with the person's skin.

It is manifest that the hazards of hosing are not intentionally visited on any victim. Nevertheless, it is the case that large caseloads and near-crisis conditions can distract the attention of those who are in charge of the immediate operation of convective treatment systems. In such circumstances, the practitioner may be unaware of the development of conditions that pose a hazard of burns, or may be forgetful of known conditions that require close and constant attention. Accordingly, significant benefits would be realized by safety provisions that operate to reduce the risk of harm that can arise during the operation of convective treatment systems. Especially desirable are measures that would warn the practitioner when the supply duct is separated from the convective device while the air duct is still being supplied with pressurized, warmed air.

The assignee of this application has designed safety provisions that reduce the risk of burns by modulating the operation of a blower in response to changes in the integrity of the connection between the air duct and the convective device. These provisions are set out in U.S. Pat. No. 6,126,681, a continuation-in-part thereof, U.S. patent application Ser. No. 09/546,078, a divisional thereof U.S. patent application Ser. No. 10/024,387 and a continuation-in-part U.S. patent application Ser. No. 10/131,068, all of which are incorporated herein by this reference.

Nevertheless, there is an immediate need for additional measures in convective treatment technology to quickly, effectively, and automatically warn of a potentially unsafe condition in which the distal end of the air supply duct is not connected, or not connected completely, to a convective device while pressurized air is still flowing through the duct.

BRIEF SUMMARY OF INVENTION

It is an object of this invention to automatically sound a warning of or otherwise audibly indicate a condition where an air supply duct that is still conducting pressurized air is not connected to a convective device.

A further object of this invention is provision of a wind-actuated instrument for sounding the warning which does not interfere with the normal operation of a convective device when properly attached to the air supply duct.

The invention is based on the critical realization that there exists an interface in a convective treatment system where measures can be implemented to sound a warning or provide an audible indication when the air supply duct is disconnected, uncoupled, or detached from the convective device under the condition that pressurized air is still flowing through the duct. The interface is where the connection, coupling, or attachment of the air supply duct with the convective device is made. At this interface, an interface device with a wind-actuated instrument is provided that sounds a warning, generates an audible indication or provides an alarm when the air supply duct is disconnected, uncoupled, or detached from the convective device and pressurized air is still flowing through the air supply duct. In addition, the interface device may also reduce, restrict or stop the flow of air through the air supply duct when the end is disconnected, uncoupled, or detached from the convective device.

BRIEF DESCRIPTION OF THE DRAWINGS

FIG. 1B is a magnified partial perspective view of a portion of a convective device where an inlet port is located, with an end of an air hose positioned to received in the inlet port;

FIGS. 2A through 2D illustrate one embodiment of the invention;

FIG. 3 is an exploded view of the interface device according to another embodiment of the invention.

FIG. 4 illustrates the interface device of FIG. 3 in the closed position;

FIG. 5 illustrates the interface device of FIG. 3 prior to attachment to an inlet port;

FIG. 6 illustrates the interface device of FIG. 3 attached to the inlet port;

DETAILED DESCRIPTION OF THE EMBODIMENTS

Figure 1A:
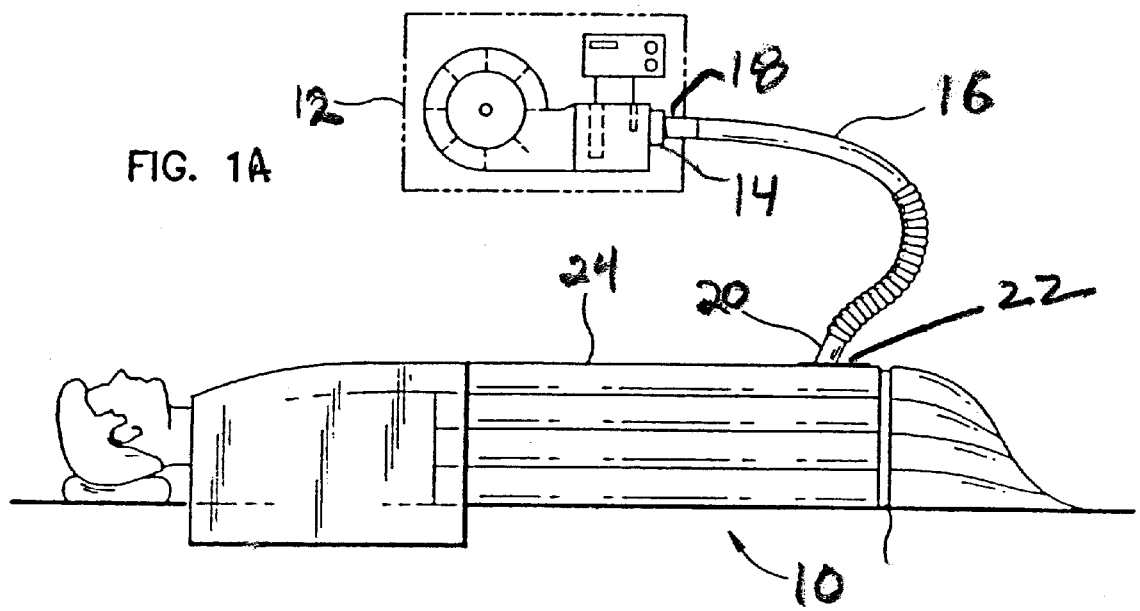
FIGS. 1A and 1B illustrate a convective treatment system in which the invention may be deployed.

In this description, a convective warming system will be described, together with certain elements of such a system. The elements will be denominated by terms that are selected for syntactic convenience and utility in suggesting a structure or a function. The terms are not selected, nor are they intended, to constrain or limit the range of structural and functional equivalents to which the elements, alone or in combination, are entitled.

In this regard, the terms "blower" and "convective device" are defined above. The term "air supply duct" is used in the background to denote a tubular passage through which air is pressurized by the blower and conducted from the blower to a convective device in a convective treatment system. Hereinafter, the term "air hose" will be used in place of "air supply duct" in order to convey the sense of a flexible tubular passage. The air hose has two ends, one for connection to the blower, the other for connection to the convective device. For convenience of this description, and for no other purpose, the end that is to be connected to the convective device may also be called a "distal" end. In the context of the invention, it is presumed that the air hose conducts pressurized air that is warmed; indeed the air may even be called "hot". This is intended to convey the sense that the temperature of the air has the potential to be raised to a level in a range, and that that level or any other level in the range results in a nozzle temperature that poses a risk of harm to a person if blown directly onto the person from the nozzle of the air hose, with the convective device removed.

The term "interface device" is also used in this description. In this application, an interface device is a device, an apparatus, an appliance, or any equivalent structure or means, that is located near where the connection, coupling, or attachment of the air hose with the convective device is made. The interface device includes a wind-actuated instrument that sounds an audible alarm indicating that the air hose is no longer attached to the inlet port and that pressurized air is still flowing through the air hose. Optionally, the interface device may also be provided with other means to wholly or partly close the distal end of an air hose in order to reduce, restrict, attenuate, or even stop the flow of air out of the air hose. The interface device can perform these functions without a nozzle being mounted to the end of the air hose. Alternatively, the interface device may be received on a nozzle at the end, integrated into the structure of a nozzle at the end, or may itself act also as a nozzle at the end.

The term "wind-actuated instrument" is used in this description. In this application, a wind-actuated instrument emits an audible output when activated by a flow of air. While the term whistle is used in the description, it is intended not to be limiting. Many other wind-actuated devices may be used in the practice of this invention including vibrating or oscillating reeds, membranes, objects (like a ball in a whistle), and valves, and shaped passages (like the aperture on the spout of a tea kettle), and other equivalent instruments.

The term "inlet port" is used in this description as well. Convective devices employ a variety of inlet port structures. In this application, an inlet port is any component of a convective device configured to allow for the ingress of pressurized air. Inlet ports may come in the form of sleeves, sheets flexible of material, and rigid structure with defined openings.

Figure 1B:
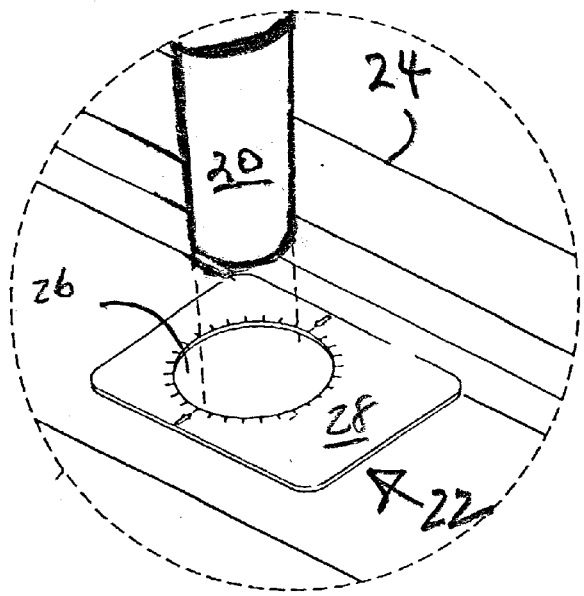

Refer to FIGS. 1A and 1B in which a convective treatment system 10 is illustrated. The elements of the system 10 include a blower 12 that aspirates air from the ambient environment, raises its temperature to a desired level, pressurizes the air above ambient pressure, and discharges the heated, pressurized air at an exhaust port 14. An air hose 16, with two ends, 18 and 20, is provided. The end 18 is connected to the exhaust port 14 and the air hose 16 conducts the heated, pressurized air to the end 20. The end 20 is connected, coupled, or joined to the inlet port 22 of a convective device 24. In this regard, the equivalent action from the point of view of the convective device 24 is that the end 20 is received in, or by, or near the inlet port 22. When the end 20 and the inlet port 22 are thus brought together, the heated, pressurized air is conducted through or out of the end 20 into the convective device 24.

A representative convective device with an inlet port is described in in the assignee's U.S. Pat. No. 6,309,408, which is incorporated by this reference. The convective device 24 and its associated inlet port 22 may be understood with reference to the '408 patent, in which an inflatable device has an opening around which is mounted a relatively stiff sheet of cardboard material. The sheet of cardboard material has an opening that is aligned with the opening in the inflatable device. The sheet provides structure to receive, retain and support the end or nozzle of an air hose in an inlet port. This arrangement, shown in FIGS. 15 and 16 of the '408 patent, is instructive in understanding the embodiments which are described below.

Completing the description of the system 10, with reference to the '408 patent as an instructive example, heated, pressurized air is conducted into the convective device 24 which conveys the air from the inlet port 22 into its interior, imposing a heat loss that reduces the temperature level of the air, and extravises the heated, pressurized air through one or more surfaces of the convective device 24. The system 10 thus delivers thermally-regulated air to the convective device 24, and the device distributes the thermally-regulated air around a person or a specific body area of the person.

In order to afford protection from injury that could result should the end 20 become separated from the inlet port 22, either by accident or by intentional action, the incorporated applications describe embodiments of an interface device that controls the interface between the inlet port 22 and the end 20. When the end 20 is connected, coupled, or joined to the inlet port 22, the interface device operates to allow pressurized, thermally-regulated air to flow through the end 20 into the convective device 24. In this invention, when the end 20 is disconnected, uncoupled, or separated from the inlet port 22 while pressurized air is still flowing, the interface device sounds an audible alarm or warning of this condition. Optionally, in addition to the audible alarm, the interface device may also operate to wholly or partly close the end 20 of the air hose 16 in order to reduce, restrict, attenuate, or even stop the flow of air through the end 20 when disconnected, uncoupled, or separated from the inlet port 22. A representative example of an interface device that wholly or partly closes the end in order to reduce, restrict, attenuate, or even stop the flow of air through the end when disconnected, uncoupled, or separated from the inlet port is described in detail in the assignee's U.S. patent application Ser. No. 10/131,068, which is incorporated by this reference. Some or all of the interface devices disclosed in U.S. patent application Ser. No. 10/131,068 could accommodate the audible indicator or alarm. Refer now to the remaining drawings, which illustrate various embodiments of the interface device.

Figure 2B:
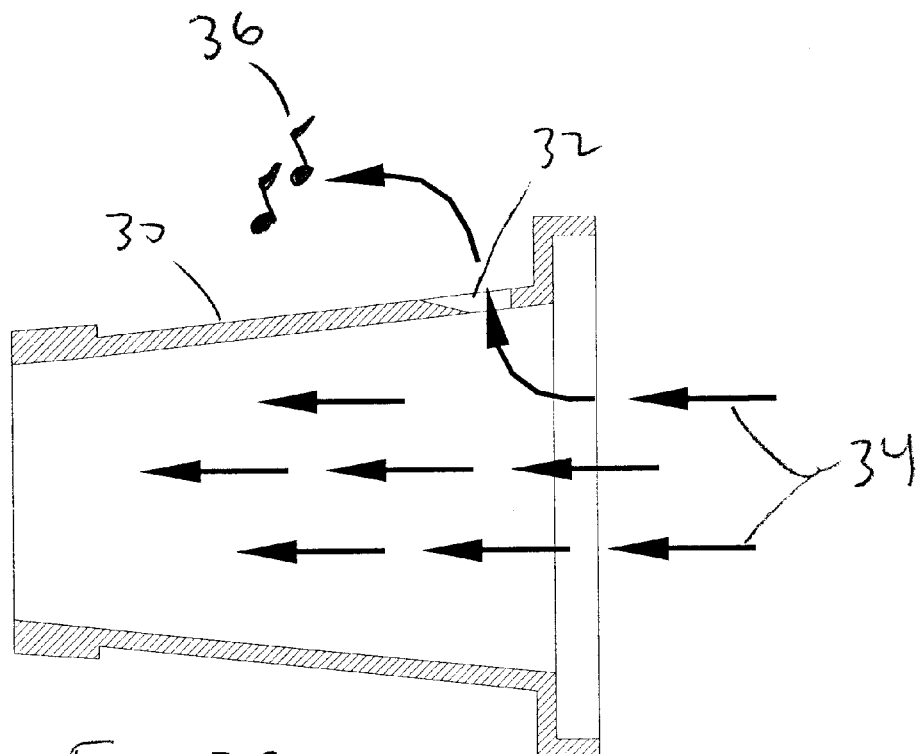
Figure 2D:
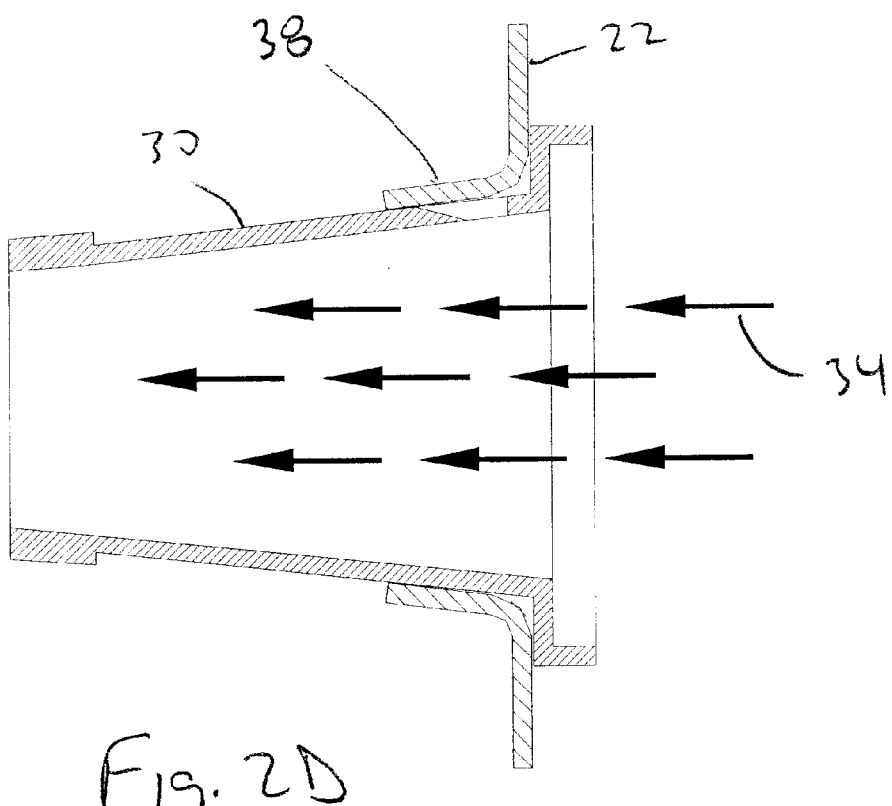

In FIGS. 2A through 2D, an interface device that exemplifies this invention is illustrated. The end 20 of the air hose 16 terminates with an interface device 30. In this embodiment, the interface device 30 includes a wind-actuated instrument 32, such as a whistle or equivalent element, to sound an audible alarm. Referring to FIGS. 2A and 2B, when the end 20 is not connected or is separated from the inlet port 22 while pressurized air 34 is flowing, the wind-actuated instrument 32 is operated by the pressurized air to sound, generate, provide, or otherwise issue an audible alarm or warning 36. The audible alarm 36 indicating to the user that the air hose 16 is not connected or has disconnected from the inlet port 22. Referring now to FIGS. 2C and 2D, the end 20 is connected to the inlet port 22. Assuming for illustration that the inlet port 22 discussed above includes an inlet port structure such as that disclosed in U.S. Pat. No. 6,309,408, it would include a sheet 28 of flexible, somewhat deformable material (such as cardboard) in which a port opening 26 is provided. In this case, the slits about the perimeter of the inlet port 26 form a plurality of fingers 38. The fingers 38 allow the port to accommodate the end or nozzle of the inflation hose which is slightly larger in outside diameter than the inner diameter of the port. As the end 20 is inserted into the inlet port 26, the fingers 38 spread apart to allow the insertion of the interface device 30. The fingers 38 are long enough to cover the wind-actuated instrument 32 when the end 20 is coupled to the inlet port 26. When coupled correctly, the fingers 38 block the flow of pressurized air through the wind-actuated instrument 32. The interface device 30 may be a separate component or may be integral with the end 20 of the air hose. In addition, the wind-actuated instrument 32 may be a separate component, may be integral with the interface device 30 or may be integral in the end 20 of the air hose. It is contemplated that the inlet port may instead be a sleeve obviating the need for fingers to occlude the flow of air as the sleeve can be drawn up to cover the wind actuated instrument.

FIG. 3 shows another embodiment of the interface device with a wind-actuated instrument that may also include a shutter. In this case, when the end 20 and the inlet port 22 are brought together the shutter opens (or, is opened) to permit pressurized air to flow out of the end 20 into the convective device. This may be considered the safe position. Likewise, when the end 20 is separated from the inlet port 22, the audible alarm is generated while the shutter closes (or, is closed), to reduce, restrict, or prevent the flow of air out of the end 20. This may be considered the alarm position.

In the example set forth here to illustrate the invention, the interface device 100 includes an end piece 102 comprising a tubular section 104 and a cylinder section 106, the tubular section 104 bisecting the cylinder section 106 at 90 degrees, the tubular section 104 in fluid communication with the cylinder section 106. A generally triangular opening 108 is disposed generally in the center of the cylinder section 106 diametrically opposite the tubular section 104. An elongate slot 110 opens into the periphery of the opening 108 and an arcuate lip 112 is provided adjacent the periphery of the opening 108, opposite the slot 110. The elongated slot 110 has a closed end 110a. A wind-actuated instrument may be mounted, seated or received in the interface device 100; it may be attached, connected, or coupled to the interface device; or, it may be formed integrally therewith. In the illustrative example being described, the instrument is embodied as a whistle 114 that is provided in the cylinder section 106 near the opening 108. The end piece 102 is preferably a unitary element formed, possibly, by molding a durable plastic. The end piece 102 is assembled to an annular collar 26 on the end 20, for example by threaded screws that extend through the tubular section 104 into the annular collar 26, although other modes of attachment are possible. A first end cap 116 is designed to sealingly attach to a first end 118 of the cylinder section 106 and a second end cap 120 is designed to sealingly attach to a second end 122 of the cylinder section 106. When assembled in this manner, the opening 108 and whistle 114 permit pressurized air to flow out of the end 20.

The interface device 100 further includes a moveable cylindrical shutter 124 having a generally cylindrical shape that corresponds to the cylindrical shape of the cylindrical section 106. The external diameter of the shutter 124 is less that the internal diameter of the cylindrical section 106 so that when the shutter 124 is received in the cylindrical section 106 it can rotate or be rotated in the cylindrical section about an axis it shares with the cylindrical section. The length of the shutter 124 is less than the length of the cylindrical section 106 so that end caps 116 and 120 will not interfere with the shutter rotation. The shutter 124 may be formed of a hard plastic. The shutter 124 includes an inlet opening 126, a triangular outlet opening 128 and a whistle opening 130. The opening 128 is generally the same size and shape of opening 108. An arcuate lip 132 is provided adjacent to the periphery of the opening 128 and a trunnion 134 is mounted on and projecting outwardly from the shutter 124. Both the arcuate lip 132 and the trunnion 134 are sized to fit in and extend through the elongate slot 110. Internal to the shutter 124 is an air diverter 135 that either diverts air to the whistle 114 or blocks that air from the whistle 114, depending on the position of the shutter 124 within the end piece 102. When air is diverted to the whistle 114, the shutter 124 is considered in the alarm position and the whistle 114 makes an audible indication or alarm. When air is blocked from the whistle 114, the shutter 124 is considered in the open or safe position.

FIG. 4 shows the interface device 100 in the closed position. The shutter 124 is rotated by moving trunnion 134 toward the closed end 110a of the elongate slot 110. In this position, opening 128 of the shutter 124 is not completely aligned with opening 108 of the end piece 102 some air will be divert by the air diverter 135 to the whistle 114. This can also be seen in FIGS. 7 and 8, which will be described below. FIG. 5 shows the interface device 100 prior to being attached to the inlet port 22. The shutter 124 is rotated toward an open position by moving trunnion 134 away from the closed end 110a of the elongated slot 110 until the arcuate lips 112 and 132 fit in the opening 26 of the inlet port 22. Once the arcuate lips 112 and 132 are inserted through the opening 26, the shutter 124 is then rotated in the opposite direction by moving trunnion 134 toward the closed end 110a of the elongate slot 110 until the arcuate lips 112 and 132 engage the edges 26a and 26b of the inlet port 22. This will lock the interface device 100 to the inlet port 22, as shown in FIG. 6. The interface device 100 is then in the open position with the opening 128 of the shutter 124 aligned with opening 108 and no air is diverted to the whistle 114. This can also be seen in FIGS. 9 and 10, which will be described below.

As thus far described, the interface device 100 can be operated manually by moving the trunnion 134 in the elongate slot 110. The self-actuated operation of the interface device 100 can be understood with reference to FIG. 3. A spring 136 is shown having a first end 138 and a second end 140. A tab 142 is on one end of the shutter 124 that engages spring first end 138. One such engagement is a hole 144. The second end 140 of the spring 136 is placed in a hole 146 in an end cap 120. When in place, the spring 136 acts between the shutter 124 and the cylindrical section 106 by urging the shutter 124 to closed position, where the trunnion 134 is rotated toward the closed end 110a. When the trunnion 134 contacts the closed end 110a, this stops the shutter 124 at the position where the opening 128 is not completely aligned with opening 108 so that any air flow would be reduced, attenuated, restricted or blocked and the air diverter 135 diverts some air to the whistle 114. Manual engagement of the trunnion 134 with a force in the opposite direction moves the trunnion 134 away from the closed end 110a and rotates the shutter 124 to a position where the alignment of the openings provide at least one aperture through the interface device 100 that is in fluid communication with end 20 and permits air flow from the end 20 though the interface device 100.

A self-actuating operation of the interface device 100 can now be described. To bring the end 20 together with the inlet port 22, the shutter 124 is rotated by pressure applied against the trunnion 134. With the shutter 124 held in this position, the interface device 100 is brought against the inlet port 22, with the arcuate lips 112 and 132 extending through the port opening 26. When the pressure is taken off the trunnion 134, a force by the spring 136 urges the arcuate lips 112 and 132 into engagement against the periphery 26a and 26b of the port opening 26. This keeps the shutter 124 in the position at which pressurized air flows out of the end 20, through the inlet port 22 and no air is diverted to the whistle 114. The end 20 is separated from the inlet port 22 by sliding the trunnion 134 away from end 110a. This disengages the arcuate lips 112 and 132 from the periphery 26a and 26b of the port opening 26. Once separated, the spring 136 urges the shutter 124 to be returned to the closed position to reduce, restrict, or prevent the flow of air out of the end 20, and the air diverter 135 diverts air to the whistle 114 to produce an audible indication or alarm that the end 20 is separated from the inlet port 22.

The operation of the interface device 100 with respect to the interface between the end 20 of the air hose 16 and the inlet port 22 can be understood with reference to FIGS. 5, 6, 9 and 10. Assuming again for illustration that the inlet port 22 includes an inlet port structure such as that disclosed in U.S. Pat. No. 6,309,408, it would include a sheet 28 of flexible, somewhat deformable material (such as cardboard) in which a port opening 26 is provided. It should be understood that the sheet 28 and the opening 26 may be many different shapes, for example, circular shape, as shown in FIG. 1B, FIGS. 2A–2D, or triangular shape, as shown in FIG. 4. The interface device 100 is mounted to the end 20 of the air hose 16, as described above.

Figure 7:
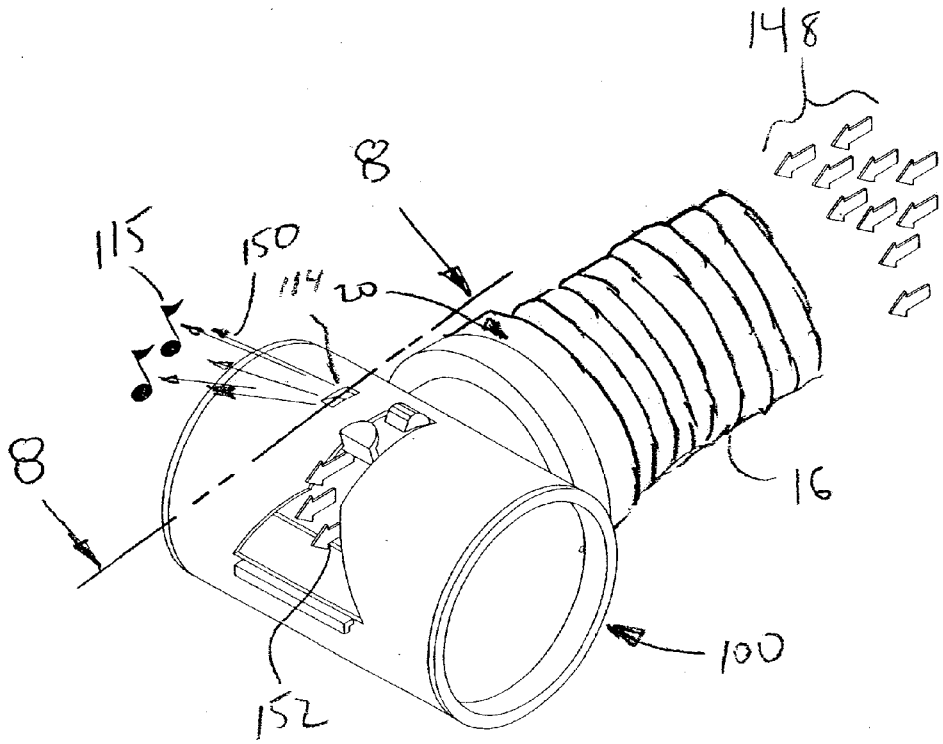
FIG. 7 illustrates the interface device of FIG. 3 when disconnected from the inlet port (closed position) with air is flowing, sounding the audible alarm.
Figure 8:
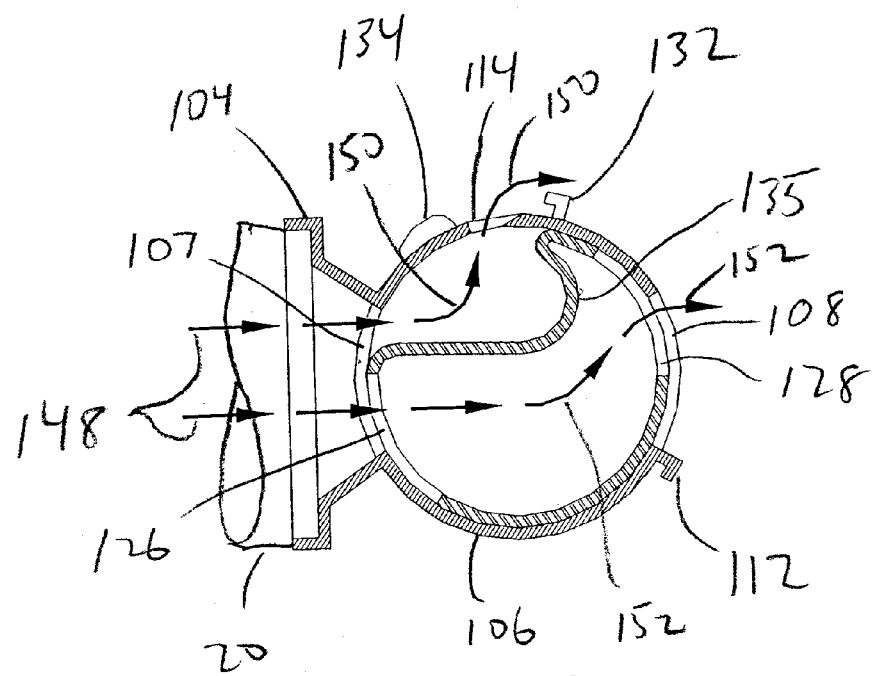
FIG. 8 is a sectional view of FIG. 7.

FIGS. 7 and 8 show the interface device 100 in the closed position, the openings in the interface device are not aligned, the flow of air is reduced or restricted and the air diverter 135 diverts some air toward the whistle 114. Air 148 flows in the air hose 16 into the interface device 100 located on end 20. In this closed position, the air diverter 135 in the interface device 100 separates the flowing air 148 into two components. A first air portion 150 is diverted to the whistle 114 and an audible alarm or whistle 115 is sounded, indicating improper operation of the equipment. A second air portion 152 continues through the interface device 100, exiting through the non-aligned openings. In other embodiments, this second air portion 152 may be prevented or blocked from flowing out of the end 20.

Figure 9:
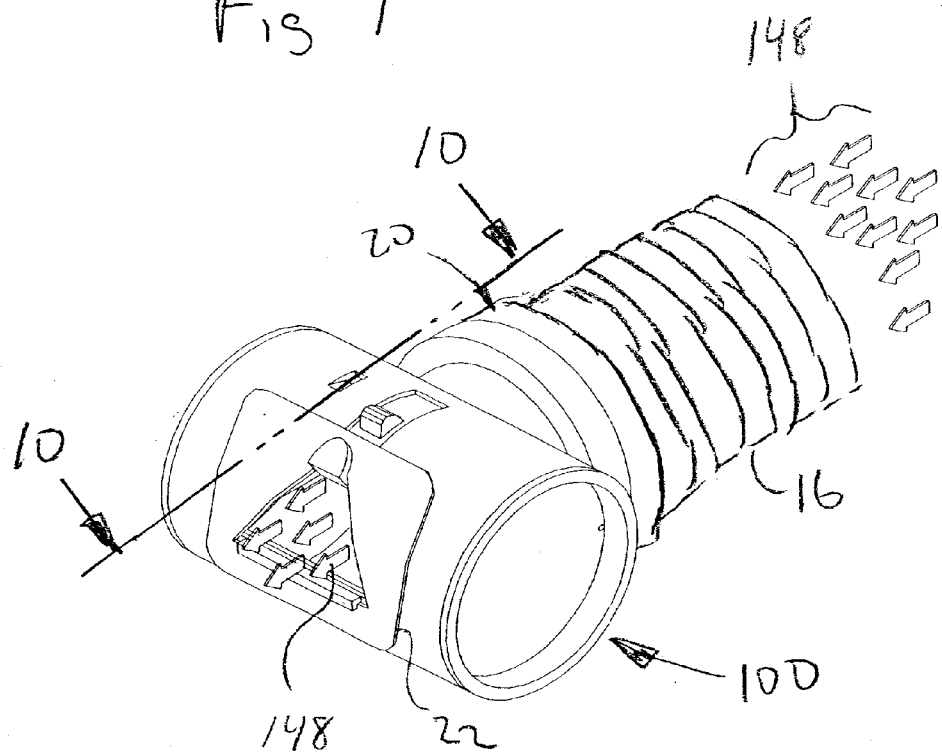
FIG. 9 illustrates the interface device of FIG. 3 when connected to the inlet port (open position) with air is flowing.
Figure 10:
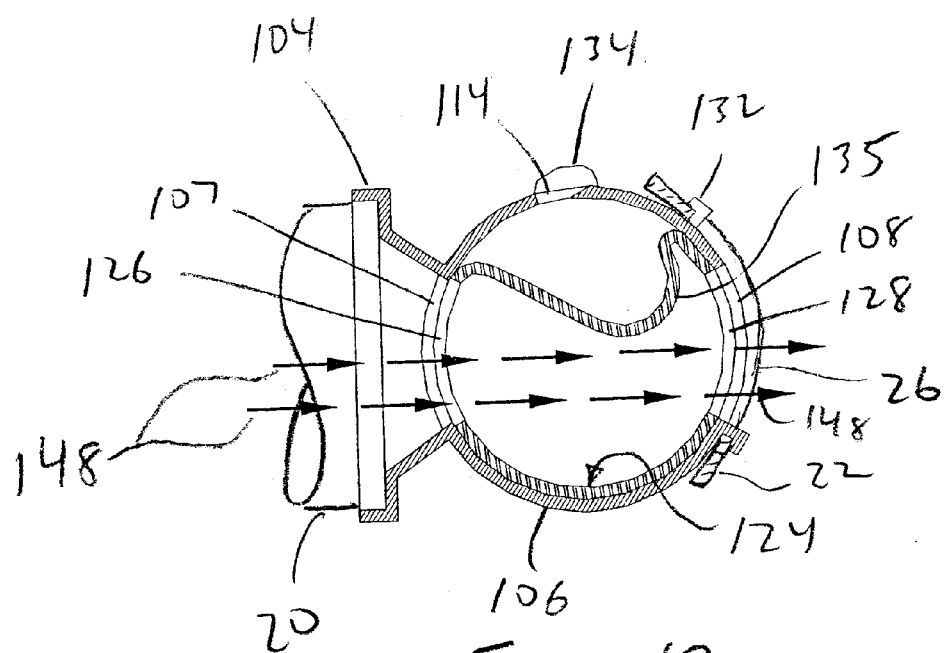
FIG. 10 is a sectional view of FIG. 9.

FIGS. 9 and 10 show the interface device 100 in the open position. The end 20 is joined with the inlet port 22 by rotating the shutter 124 and attaching the interface device 100 to the inlet port 22, as described above. In the open position, the openings in the interface device 100 and inlet port 22 are aligned. Air 148 flows in the air hose 16 into the interface device 100 located on end 20. In this position, the air diverter 135 blocks from flowing to the whistle 115, so no audible indication is sounded. The air 148 continues through the interface device 100 and the inlet port 22 into the convective device 24. In this embodiment, the alignment of the openings provides a path through the interface device 100 that is in fluid communication with the end 20 an permits air to flow from the end 20, through the interface device 100, at the relatively high rate.

What is claimed is:

1. A combination for use in a convective system, comprising:
   an air hose with an end for coupling to a convective thermal device;
   a wind-actuated instrument near the end for providing an audible indication of pressurized air through the end;
   an interface device having an air inlet for coupling to the end and an air outlet for coupling to a convective thermal device;
   in which the wind-actuated instrument is on the interface device; and
   a shutter in the interface device for moving to a safe position and to an alarm position, the safe position corresponding to coupling of the end to a convective thermal device and the alarm position corresponding to disconnection of the end from a convective thermal device.

2. The combination of claim 1 in which the shutter closes the air outlet at the alarm position.

3. The combination of claim 1, further comprising an air diverter, the air diverter being mounted on the shutter for diverting pressurized air to the wind-actuated instrument when the shutter is at the alarm position.

4. The combination of claim 1, in which the wind-actuated instrument is a whistle.

5. A combination for use with a convective thermal device comprising:
   a blower for providing pressurized air;
   an air hose with a first end for coupling to the blower and a second end for coupling to the convective thermal device;
   a wind-actuated instrument mounted near the second end of the air hose to provide an audible indication of a flow of pressurized air through the air hose;
   an interface device having an air inlet for coupling to the air hose and an air outlet for coupling to the convective thermal device, in which the wind-actuated instrument is disposed on the interface device; and
   a shutter positioned in the interface device, the shutter for moving from a safe position to an alarm position, the safe position corresponding to connection of the second end to the convective thermal device and the alarm position corresponding to disconnection of the second end from the convective thermal device.

6. The combination of claim 5 in which moving the shutter to the alarm position closes the air outlet.

7. The combination of claim 6, in which the interface device acts to keep the second end open when the second end is coupled to the convective thermal device.

8. The combination of claim 5, in which the wind-actuated instrument is a whistle.

9. A combination for controlling airflow out of an air hose, comprising:
   an inlet port for receiving pressurized air from an end of an air hose;
   an interface device to act between the end of the air hose and the inlet port by opening the end of the air hose when the end is received by the inlet port and closing the end of the air hose when the end of the air hose is separated from the inlet port;
   a wind-actuated instrument mounted on the interface device to audibly indicate separation of the end of the air hose from the inlet port while pressurized air is flowing through the interface device;

in which the interface device acts between the inlet port and the end of the to retain the end of the air hose at the outlet port; and, in which the interface device includes a shutter slidably disposed near the end of the air hose and moveable between a position at which the air hose is closed and a position at which the air hose is open and receivable by the inlet port.

* * * * *